United States Patent [19]

Hand et al.

[11] 4,154,814

[45] May 15, 1979

[54] THERAPEUTIC CHEWING GUM

[75] Inventors: Jimmie D. Hand, Novato; Timothy Wilson, Palo Alto, both of Calif.

[73] Assignee: EPS Chewing Gum, Inc., Novato, Calif.

[21] Appl. No.: 876,889

[22] Filed: Feb. 13, 1978

[51] Int. Cl.² ............................................. A61K 9/68
[52] U.S. Cl. ..................................... 424/48; 424/153
[58] Field of Search ................................ 424/48, 153

[56] References Cited

U.S. PATENT DOCUMENTS

| | | | |
|---|---|---|---|
| 2,224,252 | 12/1940 | Callaway | 426/626 |
| 2,631,119 | 3/1953 | Ferguson | 424/48 |
| 3,657,424 | 4/1972 | Aktins et al. | 424/153 |
| 3,676,553 | 7/1972 | Reynolds | 424/128 |
| 4,088,788 | 5/1978 | Ream et al. | 436/3 |

*Primary Examiner*—Donald G. Daus
*Assistant Examiner*—M. C. Eakin
*Attorney, Agent, or Firm*—Melvin R. Stidham

[57] ABSTRACT

A therapeutic chewing gum composition orally utilizable to maintain the minerals balance of human physiological fluids during strenuous activity comprising an insoluble gum base having bound therein from about 2 to about 6 percent by weight of sodium chloride and from about 0.1 to about 0.5 percent by weight of potassium chloride; wherein the relative weight ratio of sodium chloride to potassium chloride is at least about 3:1.

10 Claims, No Drawings

THERAPEUTIC CHEWING GUM

BACKGROUND OF THE INVENTION

This invention concerns a therapeutic chewing gum which can be used to maintain the minerals balance of human physiological fluids, particularly during strenuous physical activity. The chewing gum composition of this invention, comprising relatively high concentrations of sodium and potassium salts in a critical weight ratio, when orally utilized supplements the minerals assimilated by physiological fluids.

During periods of unusual physical or mental activity the human body may lose as much as 10 percent of its total fluids content. The principal source of body fluids is the bloodstream. Consequently, after a heavy loss of fluids there may be a substantial reduction in the blood supply to the muscles. A reduction in the blood supply causes muscles to cramp as waste products accumulate. A reduction in the blood supply also causes the body temperature to rise due to reduced circulation at the skin surface resulting in heat exhaustion.

Lost fluid can be replaced by drinking. As fluid is put into the stomach, the body responds by preparing the fluid for assimilation. This process requires the addition of sodium and potassium salts. Fluids are ready for assimilation when they reach about a one percent saline solution. If there is an insufficient supply of sodium and potassium salts in the stomach, the body supplies these minerals by pulling them away from existing body minerals.

In order to avoid stressing the existing minerals content of the body, it is a common practice to ingest supplemental quantities of the salts as well as fluid. Since the salts are readily soluble, they are almost immediately dissolved and assimilated in the body. However, in order to maintain a normal balance between the minerals' supply to the stomach and the body's assimilation of the minerals, it is desirable to avoid an instantaneous ingestion of a large quantity of salt followed by a prolonged period of exertion. It is preferable to maintain the minerals balance by a more or less continuous supply of minerals to the stomach. One way which has been suggested to supply minerals to the body, without the need to ingest large doses of salts, is by drinking fluids which already contain the desired concentration of salts. While this suggestion is more satisfactory than simply ingesting tablets of salt, it has shortcomings. In particular, the user loses control over the content of salt, and must consume fluids sometimes under physically difficult circumstances.

Accordingly, there is a definite need to provide a means of easily maintaining the minerals balance of human physiological fluids without the need to spontaneously ingest distastefully large doses of sodium and potassium salts. The therapeutic chewing gum composition of this invention fulfills this need.

Chewing gum compositions are well known. In fact, various therapeutic agents have been suggested as adjuvants for chewing gum. For instance, U.S. Pat. No. 3,932,608 granted Jan. 13, 1976 to Anderson et al describes food compositions, such as chewing gum, containing cariostatic and nutritional fortification agents; U.S. Pat. No. 3,075,884 granted Jan. 29, 1963 to Bilotti et al describes chewing gum compositions containing enzymes, antacids, vitamins, and the like; and U.S. Pat. No. 3,655,866 granted Apr. 11, 1972 to /Bilotti describes a sugarless gum containing dicalcium phosphate dihydrate.

Heretofore, chewing gum has not been considered as a suitable vehicle for delivery of minerals, particularly sodium and potassium salts, to the stomach. The supplemental ingestion of sodium and potassium salts present difficult aesthetic problems. Effective concentrations of salts, particularly the combination of sodium and potassium salts, have an extremely objectionable taste. Masking the objectionable taste, while continuously supplying the salts is a difficult problem. Flavorings tend to dissipate more readily than the taste of the salts. Moreover, sodium and potassium salts readily absorb moisture from their environment and accordingly leach out of many solid ingestible vehicles.

U.S. Pat. No. 2,631,119 discloses a therapeutic appetite satiant composition which can be taken using a chewing gum vehicle. The therapeutic composition contains sodium chloride. The synergistic effect of additional constituents, such as sodium glutamate, on the taste of the composition is particularly noted. In order to overcome this problem, protein hydrolysate is added and only small quantities of the composition are added to each slab of gum. While such a composition delivered in relatively small quantities may provide appetite satiant properties, the use of small concentrations of sodium salt alone is insufficient to provide balanced mineral supplementation to the human body.

SUMMARY OF THE INVENTION

It has now been found that minerals, particularly sodium and potassium chlorides, can be supplied to the stomach for assimilation into body fluids by a therapeutic chewing gum composition comprising an insoluble gum base containing from 2 to 6 percent by weight of sodium chloride and from 0.1 to 0.5 percent by weight of potassium chloride, wherein the weight ratio of sodium chloride to potassium chloride is at least about 3:1.

DETAILED DESCRIPTION OF THE INVENTION

Among other factors, the invention described in detail below is based upon the unexpected discovery that minerals such as sodium and potassium chlorides can be effectively delivered to the human stomach for assimilation into body fluids thereby maintaining a balanced minerals content by a chewing gum composition which comprises an insoluble gum base containing select concentrations of sodium and potassium chlorides in a critical weight ratio. In particular, it has been found that the objectionable salty taste of chewing gum compositions comprising relatively high concentrations of sodium and potassium chlorides can be overcome if the weight ratio of sodium chloride to potassium chloride is at least 3:1, preferably 5:1, and most preferably 10:1.

Insoluble chewing gum bases suitable for use as the vehicle for delivering sodium and potassium chlorides in accordance with this invention are well known in the art, and are commercially available. Generally, chewing gum bases comprise a resin or wax, such as chicle, jelutong, guttakay, rubber, or certain synthetic waxes or resins, compounded with sugars, such as sucrose, glucose as corn syrup, dextrose, fructose, and/or artificial sweeteners such as cyclamates or saccharin, as well as softeners, fillers, colorings, and flavorings. For example, suitable chewing gum bases have the following general formulation:

| Ingredient | Weight Percent |
| --- | --- |
| wax or resin | 10–25 |
| sucrose | 50–75 |
| glucose | 15–25 |
| dextrose | 1–10 |
| fructose | 1–5 |
| softeners, fillers, colorings, flavorings, vitamins, etc. | 1–5 |

Particularly preferred chewing gum bases have the general formula:

| Ingredient | Weight Percent |
| --- | --- |
| wax or resin | 10–15 |
| sucrose | 55–65 |
| glucose | 15–20 |
| dextrose | 1–5 |
| fructose | 1–5 |
| softeners, fillers, colorings, flavorings, vitamins, etc. | 1–5 |

Various adjuvants to improve texture, flavor, and the like can be included in the composition. For instance, vitamins such as ascorbic acid (vitamin C), thiamine mononitrate (vitamin $B_1$), riboflavin (vitamin B2); calcium and phosphorus compounds such as calcium phosphate and magnesium phosphate; softeners such as glycerine; flavorings such as spearmint, peppermint, wintergreen, and licorice; and the like can be added.

In accordance with this invention, the chewing gum base vehicle is used to deliver therapeutic amounts of sodium and potassium chlorides to the stomach for assimilation by the body fluids. The concentration of each of these salts can vary. However, it is essential that the sodium chloride to potassium chloride weight ratio is at least about 3:1. Preferably, the sodium to potassium chlorides weight ratio will range from about 5:1 to about 20:1, most preferably from about 10:1 to 15:1. At ratios in excess of about 20:1, the amount of potassium chloride is insufficient to achieve any therapeutic benefit. At ratios below about 3:1, the relatively large amount of potassium chloride acts synergistically with the sodium chloride to create an unexceptable salty taste which cannot be effectively masked.

For instance, the concentration of sodium chloride can vary from about 2 to about 6 weight percent of the total composition. Preferably, the concentration of sodium chloride ranges from about 3 to 5 weight percent. The concentration of potassium chloride can vary from about 0.1 to about 0.5 weight percent. Preferably, the concentration of potassium chloride ranges from about 0.2 to about 0.4 weight percent.

The therapeutic chewing gum of this invention can be manufactured by heating and blending the various ingredients according to conventional techniques. The order in which the ingredients are mixed is not critical. However, it is the usual practice to prepare the base vehicle and mix the desired adjuvants and the sodium and potassium chlorides into it. In order to insure a sustained prolonged delivery of the sodium and potassium salts, homogenous blending is particularly desirable. The total mixing time of a typical formulation is about 15 to 20 minutes. After mixing the bulk formulation can be further processed into the desired shape and packaged.

In a preferred embodiment, after the therapeutic chewing gum is formulated, the final slab tablet, or ball (shape is not critical) is sealed with a moisture repellant coating. For instance, the final slabs or gum balls can be coated with a sugar solution to form a coating which resists the ambient moisture of humid storage conditions, but readily dissolved when chewed. In this way, the desicant properties of the sodium and potassium salts are nullified and the tendency of these salts to leach from the gum base is substantially eliminated. In addition, moisture proof packages further insures that the salts will not leach from the gum base.

The therapeutic benefits of the gum composition of this invention are obtained over a prolonged continuous period of time, in many instances as long as 70 minutes. During this period, sodium and potassium salts are continuously delivered to the stomach and assimilated by the body fluid. Accordingly, the gum composition is particularly useful to replace lost minerals occasioned by strenuous physical activity. For instance, the therapeutic benefits of the gum are particularly suited to athletes and firemen who are exposed to prolonged strenuous activity often under conditions which cause substantial body fluid loses. It has been found that for optimum benefits, a typical embodiment of the gum containing about 50 milligrams of sodium and potassium chloride should be consumed at the rate of about 3 to 4 pieces per hour of strenuous activity.

EXAMPLES

The following example further illustrates the formulation and use of a therapeutic chewing gum composition in accordance with this invention. The composition exemplified is a preferred embodiment. The example is not intended to limit the scope of the invention as it will suggest numerous alternative embodiments.

The following ingredients were added to a standard gum mixing kettle: commercial gum resin, sucrose, glucose, dextrose, fructose, calcium, magnesium phosphate, ascorbic acid, sodium chloride, and potassium chloride. The agitators of the mixing kettle were started and the ingredients were mixed until a homogenous blend was obtained, about 15 minutes. The mixing was stopped; the sides of the kettle were scraped; and the gum product was unloaded from the kettle, rolled into individual balls of about 1200 milligrams, and coated. Each ball of gum had the following compositions:

| Ingredient | Weight in Milligrams |
| --- | --- |
| gum resin | 130 |
| sucrose | 750 |
| glucose | 190 |
| dextrose | 50 |
| fructose | 20 |
| calcium | 4 |
| magnesium phosphate | 2 |
| ascorbic acid | 6 |
| sodium chloride | 50 |
| potassium chloride | 4 |

Samples of the gum balls were provided members of a professional football team during a strenuous two-hour practice session. It was noted by their Head Athletic Trainer that those players who had chewed about 5 balls of gum during the session had no significant muscle cramping or heat exhaustion difficulties.

What is claimed is:

1. A therapeutic chewing gum composition comprising an insoluble gum base vehicle having bound therein from about 2 precent by weight to about 6 percent by weight of sodium chloride and from about 0.1 percent by weight to about 0.5 percent by weight of potassium chloride, wherein the weight ratio of sodium chloride to potassium chloride is at least about 3:1.

2. A composition in accordance with claim 1 wherein the vehicle has bound therein from about 3 percent by weight to about 5 percent by weight of sodium chloride and from about 0.2 percent by weight to about 0.4 percent by weight of potassium chloride.

3. A composition in accordance with claim 1 wherein the weight ratio of sodium chloride to potassium chloride is at least about 5:1.

4. A composition in accordance with claim 1 wherein the weight ratio of sodium chloride to potassium chloride is at least about 10:1.

5. A composition in accordance with claim 1 wherein the weight ratio of sodium chloride to potassium chloride is from about 5:1 to about 20:1.

6. A composition in accordance with claim 1 wherein the weight ratio of sodium chloride to potassium chloride is from about 10:1 to about 15:1.

7. A composition according to claim 1 wherein the base vehicle comprises from about 10 to 25 weight percent wax or resin, from about 50 to 75 weight percent sucrose, from about 15 to 25 glucose, from about 1 to 10 weight percent dextrose, and from about 1 to 5 weight percent fructose.

8. A composition according to claim 7 wherein the base vehicle comprises from about 10 to 15 weight percent wax or resin, from about 55 to 65 weight percent sucrose, from about 15 to 20 weight percent glucose, from about 1 to 5 weight percent dextrose, and from about 1 to 5 weight percent fructose.

9. A composition according to claim 1 further characterized by the presence of from about 1 to 5 weight percent of an adjuvant selected from the group consisting of softeners, fillers, coloring agents, flavorings, vitamins, nutrients, and mixtures thereof.

10. A therapeutic chewing gum composition comprising about 10 percent by weight of gum waxes or resins, about 60 percent by weight of sucrose, about 15 percent by weight of glucose, about 5 percent by weight of dextrose, about 2 percent by weight of fructose, about 0.5 percent by weight of ascorbic acid, about 0.5 percent by weight of calcium, about 0.5 percent by weight of magnesium phosphate, about 0.3 percent by weight of potassium chloride, and about 4 percent by weight of sodium chloride.

* * * * *